United States Patent [19]
Rader et al.

[11] Patent Number: 5,400,758
[45] Date of Patent: Mar. 28, 1995

[54] ALCOHOL CONCENTRATION SENSOR FOR AUTOMOTIVE FUELS

[75] Inventors: Richard K. Rader, West Bloomfield, Mich.; Rodney E. Barr, Cary; Carl R. Vogt, Raleigh, both of N.C.; John J. C. Kopera, Rochester Hills, Mich.

[73] Assignees: Borg-Warner Automotive, Inc., Sterling Heights; Chrysler Corporation, Highland Park, both of Mich.

[21] Appl. No.: 125,089

[22] Filed: Sep. 21, 1993

Related U.S. Application Data

[63] Continuation of Ser. No. 844,958, Feb. 28, 1992, Pat. No. 5,255,656, which is a continuation of Ser. No. 722,013, Jun. 27, 1991, abandoned.

[51] Int. Cl.⁶ .............................................. F02M 51/00
[52] U.S. Cl. ...................................... 123/494; 123/1 A
[58] Field of Search ............... 123/494, 109, 478, 575, 123/417, 497; 73/116, 861.08, 304; 331/65; 324/61 P, 60, 58.5

[56] References Cited

U.S. PATENT DOCUMENTS

| | | | |
|---|---|---|---|
| 3,816,811 | 6/1974 | Cmelik | 324/61 P |
| 4,001,676 | 1/1977 | Hile et al. | 324/60 |
| 4,323,046 | 4/1982 | Barber | 123/575 |
| 4,438,749 | 3/1984 | Schwippert | 123/494 |
| 4,453,125 | 6/1984 | Kimura et al. | 324/58.5 |
| 4,470,300 | 9/1984 | Kobayashi | 73/116 |
| 4,676,101 | 6/1987 | Baughman | 73/304 |
| 4,706,630 | 11/1987 | Wineland et al. | 123/478 |
| 4,770,129 | 9/1988 | Miyata et al. | 123/478 |
| 4,905,655 | 3/1990 | Maekawa | 123/494 |
| 4,915,084 | 4/1990 | Gonze | 123/575 |
| 4,957,087 | 9/1990 | Ota | 123/494 |
| 4,971,015 | 11/1990 | Gonze | 123/494 |
| 4,989,570 | 2/1991 | Kuribara et al. | 123/478 |
| 4,995,367 | 2/1991 | Yamanchi et al. | 123/494 |
| 5,003,956 | 2/1991 | Iwamoto et al. | 123/494 |
| 5,014,670 | 5/1991 | Mitsumoto | 123/494 |
| 5,044,344 | 9/1991 | Tuckey et al. | 123/497 |
| 5,060,619 | 10/1991 | Sakurai et al. | 123/494 |
| 5,150,683 | 9/1992 | Depa et al. | 123/417 |

*Primary Examiner*—Raymond A. Nelli
*Attorney, Agent, or Firm*—Mark P. Calcaterra

[57] ABSTRACT

An electronic sensor (20) for measuring methanol content in gasoline fuels for automotive engines including a sensing coil (108/108') and a paired capacitance element (42,44/42', 44') that cooperates with the coil to define an oscillating circuit wherein the gasoline methanol fuel mixture is used as a dielectric for the capacitor elements of the sensor, a change in the methanol concentration in the fuel resulting in a change in the dielectric constant of the sensor (20) which results in a change in the resonant frequency of the capacitor elements (108/108', 42/44/42', 44'), and a microprocessor circuit (160) which responds to a change in the oscillating frequency to establish a control signal that may be used by an automotive powertrain controller (24) to effect appropriate adjustments in the air/fuel ratio and ignition timing for the engine (10) to compensate for variations in the methanol content of the fuel.

4 Claims, 12 Drawing Sheets

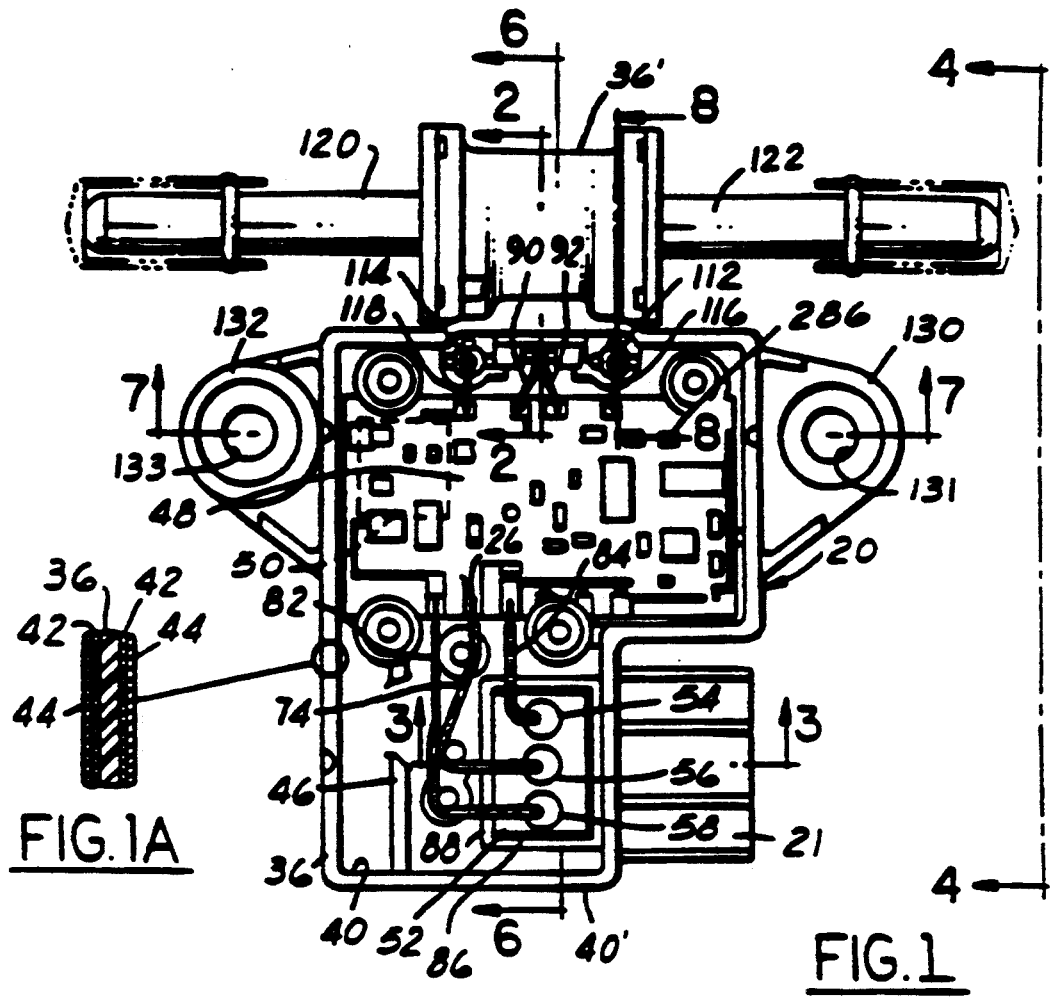
FIG.1A
FIG.1
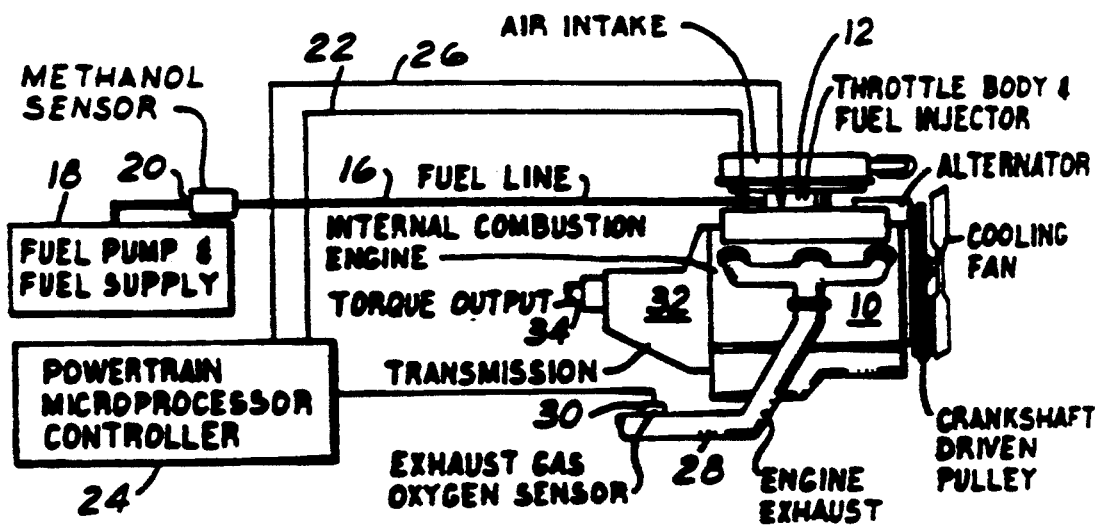
FIG.11

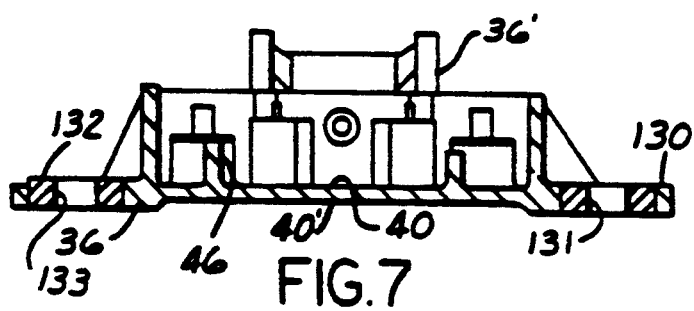
FIG.7
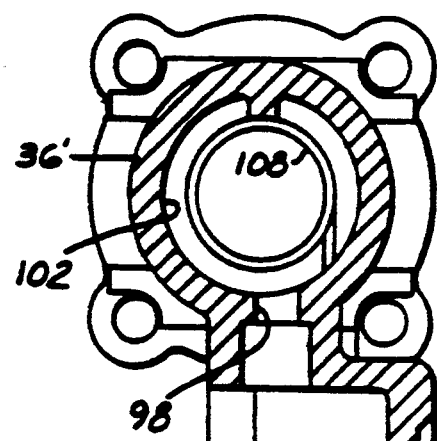
FIG.6
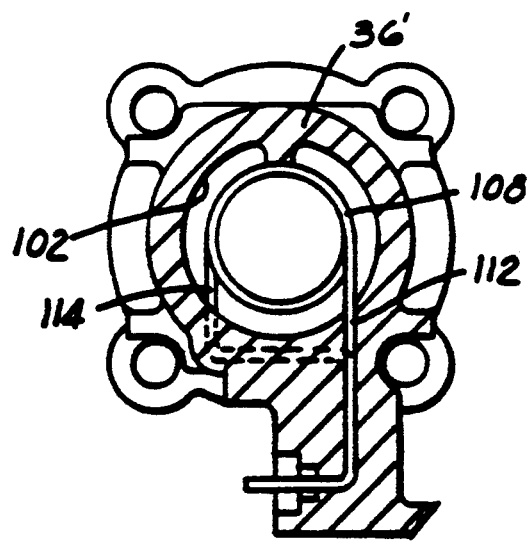
FIG.8
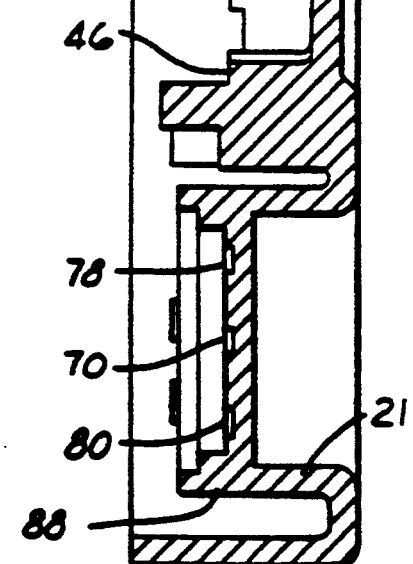

ALCOHOL CONCENTRATION SENSOR FOR AUTOMOTIVE FUELS

This is a continuation of U.S. patent application Ser. No. 07/844,958, filed Feb. 28, 1992, which is a continuation of U.S. patent application Ser. No. 07/722,013, filed Jun. 27, 1991, and now abandoned.

TECHNICAL FIELD

Our invention relates to powertrain controllers for internal combustion engines, especially vehicle engines, and to electronic sensors for the controller that provide a measurement of alcohol concentration in the engine fuel.

BACKGROUND OF THE INVENTION

Our invention is adapted to be used in a fuel system for a so-called flexible fuel vehicle, also known as an FFV. Such vehicles have been described in automotive technical literature as a possible solution to environmental concerns about the use of petroleum fuels and to marketing concerns arising from over-dependence on petroleum fuels as a source of fuel for internal combustion engines.

Methanol is considered to be an acceptable additive for gasoline fuels in the formulation of a commercially feasible gasoline/alcohol mixture for a flexible-fuel vehicle. The combustion characteristics of methanol, however, are substantially different than the combustion characteristics of gasoline. Gasoline fuels that presently are available commercially, therefore, cannot be used interchangeably with a mixture of methanol and gasoline without appropriate adjustments of the air/fuel ratio and the timing of the spark advance for spark-ignition internal combustion engines. The energy content of methanol, for example, is about half of the energy content of gasoline per unit volume. Methanol also tends to increase the cold start problems during engine cranking, especially in cold weather.

Engine controls for flexible-fuel vehicles require a design compromise between fuel performance, fuel cost and effects of methanol content on engine fuel and air mixture control and on ignition timing. A design objective in designing controls for flexible fuel vehicles is the achievement of high engine performance and stoichiometric fuel combustion efficiency with varying methanol concentrations, even with gasoline and methanol mixtures of up to 85 percent methanol.

Electronic powertrain controllers of the kind commonly used in the automotive industry are capable of adjusting engine ignition timing, fuel rate and air-fuel ratio to satisfy a variety of operating variables including vehicle speed, altitude, ambient temperature, automatic transmission ratio and throttle setting. The flexible fuel sensor of our invention is capable of providing additional information to such a powertrain controller so that the controller may compensate for variations in the concentration of methanol in the gasoline fuel as well as for other driveline variables.

A characteristic of alcohol that makes it feasible to obtain a reliable measure of alcohol concentration is its relatively high dielectric constant in comparison to the dielectric constant for gasoline. In the case of pure methanol, for example, the dielectric constant may be approximately 32, whereas in the case of gasoline the dielectric constant may be approximately 2.0. The dielectric constant for pure ethanol is about 25. These relatively wide variations make possible useful measurements by the sensor that can be reliably processed by the powertrain controller.

We are aware of prior art teachings that rely upon the use of a capacitor in the presence of a methanol gasoline fuel mixture to provide variations in the dielectric constant for the capacitor as an indication of the percentage of methanol in the mixture. One such teaching is shown in prior art U.S. Pat. Nos. 4,971,015 and 4,915,084. These patents describe a sensor that comprises a capacitor situated in a fuel line of an internal combustion engine. One capacitor element of the sensor is located in the fuel flow path, and a companion capacitor element surrounds it and defines a part of the fuel delivery conduit. An oscillator circuit, which is independent of the sensor, develops an oscillating voltage that drives an oscillator comprised of the capacitor and a series related resistor. The resonant frequency of the circuit changes in response to changes in the capacitance of the sensor due to changes in the dielectric constant of the fuel mixture, the latter in turn being a measure of the percentage of methanol in the fuel.

It is also known in the art to provide a so-called optical sensor for measuring alcohol concentrations in gasoline, an example being described in U.S. Pat. No. 4,438,749. Such sensors rely upon a light source and include an electronic circuit that measures the light transmission through the fuel mixture as the refractive index is adjusted depending upon the concentration of the alcohol in the fuel. Such systems are relatively undependable, however, because of variations in the light transmissibility of the fuel due to changes in the mixture that do not demand a corresponding change in air/fuel ratio.

Other prior art sensors that rely upon an oscillator circuit to detect variations in fuel mixture comprise a microwave oscillator of the kind described in U.S. Pat. No. 4,453,125, in which a capacitor circuit has a frequency that is affected by changes in the dielectric constant of the fuel blend. The attenuation of the microwave frequency is an indicator of the fuel additive content. Such systems, however, are relatively expensive and generate a relatively high electromagnetic interference level.

Another optical sensor is described in U.S. Pat. No. 4,995,367. The fuel control system of the U.S. Pat. No. '367 patent controls droplet size of fuel particles in a methanol/gasoline engine to effect efficient combustion. The system provides for adjustments in the air/fuel ratio and in ignition timing. One of the variables used by the controller is the methanol percentage for the fuel. The fuel sensor used to determine that percentage is an optical unit with a photoelectric pickup.

Another prior art methanol sensor is described in technical literature of Japan Electronic Control Systems Co., Inc. of Isesaki, Japan. This sensor, like the sensor described in the U.S. Pat. No. '084 and '015 patents mentioned above, uses concentric capacitor electrodes through which fuel is passed. A separate oscillator circuit develops a frequency that is modified by the fuel capacitor as the methanol content changes. An alcohol concentration sensor forming a part of an electronic engine fuel control is shown in U.S. Pat. No. 5,003,956, which is assigned to Japan Electronic Control Systems Co., Inc.

GENERAL DESCRIPTION OF THE INVENTION

Our sensor uses an oscillator circuit having capacitor elements that function in the presence of the fuel mixture so that the dielectric constant of the mixture will determine the oscillating frequency of the circuit. A change in capacitance of the capacitor elements will occur if the fuel mixture is altered because the fuel acts as a dielectric material for the capacitor elements in the oscillator circuit. A relationship then can be established between the capacitance variation and the composition of the mixture, the capacitance variation resulting in a change in frequency of the oscillating circuit elements for the sensor.

A sensing coil in the sensor may be placed in the fuel line at the fuel tank or at a location proximate to the engine throttle body and fuel injectors. If it is anticipated, for example, that the methanol concentration in the fuel tank will change from time to time as the tank is refilled at different fuel supply locations, it may be desirable to locate the sensor 20 as close as possible to the fuel injectors for the engine. This helps to avoid momentary problems with combustion efficiency if at a given instant the fuel in the fuel line downstream from the tank has a different methanol concentration than the methanol concentration of the fuel in the tank. Of course, the powertrain controller may be calibrated to compensate for differences between the alcohol concentrations in the fuel line at the throttle body and at the tank even if the sensor were to be located at the tank. The calibration might be simplified, however, if the powertrain microprocessor buffer memory were not required to store the sensor data prior to the change in alcohol concentration for fuel in the tank and to delay a change in engine calibration until the residual fuel in the fuel line downstream from the tank is burned by the engine. The sensor thus provides an oscillating frequency that is functionally related to the percent of methanol in the fuel mixture as the fuel enters the engine fuel controller regardless of changes in methanol content in the fuel in the fuel supply tank and regardless of the location of the sensor in the fuel system.

The sensing coil is coated in multiple layers with a polyamide-imide coating, which is a product supplied by Phelps Dodge and described in its published literature. This coating assures that the sensing coil will not be subject to corrosion caused by the methanol and it will not allow a shorting of the capacitor circuit. Reference may be made to "Modern Plastics Encyclopedia" for 1979-1980 at Pages 45 and 46, by C. J. Billerbeck, for a description of the chemistry and properties of polyamide-imide. It is generally described as a condensation polymer of trimellitic anhydride and various aromatic diamines. It has good electrical insulating properties and radiation resistance as well as chemical resistance.

The sensing coil in a first embodiment of our invention has 20 turns and has a resonant frequency of approximately 18 Mhz. The oscillator signal is transferred through an electronic circuit, including a frequency divider which divides the relatively high frequency developed by the sensor by a factor of 256 before it is distributed to a microprocessor. The microprocessor relies upon the frequency signal that is developed by the sensor and upon an integrated circuit board temperature sensor and a fuel temperature sensor to develop an output signal in accordance with a basic algorithm which will be described.

Unlike the prior art teachings, the sensor of our invention uses substantially fewer circuit elements and may be contained in a miniaturized housing with the microprocessor and related integrated circuit members in a compact assembly with economy of space within the powertrain compartment of a vehicle.

The housing is comprised of a plastic substrate on which is deposited a copper base. The plastic is treated with a catalyst to improve the adhesion property of the copper. An electroless plating process is used to deposit the copper. The copper then is covered with a nickel coating. This also may be done using the electroless process.

The nickel coating is impervious to the fuel mixture. Each of the two metallic layers is about 0.0005 inch thick. Reference may be made to literature published by Mitsui-Pahthec Corp. of Rochester, N.Y., for a description of a molding and metallizing or plating process that might be used in depositing the copper and nickel.

The metallic coating also permits an electrical connecter to be soldered directly to the housing, as will be described subsequently. This facilitates fabrication, reduces cost, and makes miniaturization of the assembly feasible.

The coating provides inherent radio frequency interference (RFI) protection, which improves the reliability of the sensor and the associated electronic circuit elements. It also reduces the degree of random background electromagnetic interference or electronic noise.

In contrast to the teachings of the U.S. Pat. Nos. '015 and '084 patents, our improved sensor relies upon the metallic coating on the plastic as one of the capacitor elements in the oscillator circuit. The sensing coil is disposed within a housing portion, which contains a copper/nickel coating, in the fuel line adjacent the engine fuel controller. Both the sensing coil and the surrounding plated portion of the housing are exposed to the fuel, which functions as a dielectric and determines the oscillating frequency of the sensor.

It is possible, of course, to rely upon a series-related, distributive, parasitic capacitance of the coil itself as a control variable to establish the control frequency of the sensor. Such distributive capacitance would result, however, in a rather insensitive sensor since it would have a low sensitivity value of only about 6 MHz. By relying upon the portion of the plated housing that surrounds the sensing coil of our improved sensor as one element of the oscillator circuit in combination with the inductance of the coil itself, the sensitivity of the sensor can be improved so that it is capable of developing a frequency range much greater than that which would exist if the housing coating were not part of the oscillator circuit. After the signal frequency is divided by a frequency divider to effect a useful input for the microprocessor, the resultant sensitivity may be six to ten times greater.

A second embodiment of our invention has a relatively low frequency oscillator including paired astable multivibrators in a network that includes the sensing coil. The oscillator produces a square wave input signal that is distributed directly to the microprocessor.

BRIEF DESCRIPTION OF THE FIGURES OF THE DRAWING

FIG. 1 is a plan view of the miniaturized sensor of our invention.

FIG. 1A is a detail sectional view of the housing wall showing the layered metallic coating.

FIG. 6 is a cross-sectional view taken along the plane of section line 2—2 of FIG. 1, but it differs from the view of FIG. 2 because parts have been omitted for purposes of clarity.

FIG. 7 is a cross-sectional view taken along the plane of section line 7—7 of FIG. 1.

FIG. 8 is a cross-sectional view taken along the plane of section line 8—8 of FIG. 1.

FIG. 11 is a schematic representation of an engine and the disposition of the powertrain controller, the fuel supply and the methanol sensor, the latter being the subject of our invention.

PARTICULAR DESCRIPTION OF THE INVENTION

Figure 2:
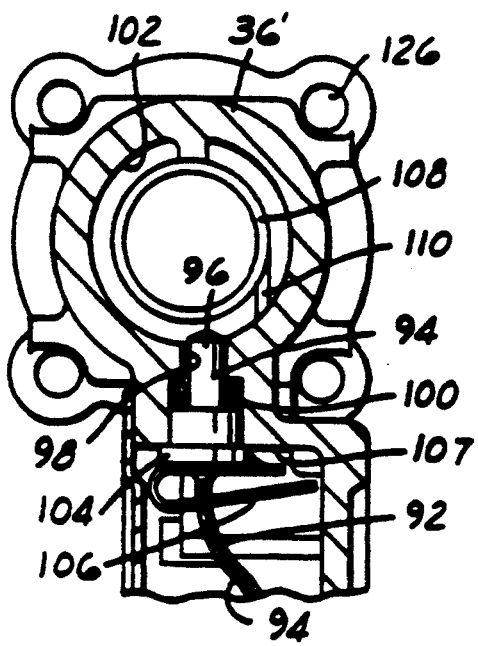
FIG. 2 is a cross-sectional view taken along the plane of section line 2—2 of FIG. 1.

Referring first to FIG. 11, the internal combustion engine 10 includes a throttle body and fuel injector 12 situated between the fuel intake manifold and an air supply, which includes air intake and air cleaner assembly 14. A fuel line 16 delivers fuel from the fuel tank or supply 18. The fuel supply includes a tank and a fuel pump for developing a fuel delivery line pressure, the pressurized fluid being delivered to methanol sensor 20 of our invention. Sensor 20 may be located in the fuel line 16 on or directly adjacent the fuel tank 18, although a location near the engine throttle body, as mentioned earlier, might be appropriate if an alcohol concentration reading is needed at a point in the fuel flow path near the fuel injectors. Sensor 20 communicates through control line 22 with powertrain microprocessor controller 24, which controls the engine spark advance and the fuel supply at the fuel injector and air intake assembly which communicates with the controller 24 through control line 26.

The engine includes an engine exhaust conduit 28, and an exhaust gas oxygen sensor 30 situated in the exhaust 28 to detect oxygen content in the exhaust. Sensor 30 provides an indication of the efficiency of the combustion process. The signal obtained from exhaust gas sensor 30 may be used as a feedback signal for correcting adjustments of the fuel injector controller as the latter responds to signals developed by the powertrain microprocessor controller 24.

The engine includes a crankshaft-driven pulley as indicated, which drives the cooling fan. A power transmission mechanism 32 delivers power from the engine crankshaft through transmission gearing (not shown) into a torque output shaft 34, which is connected through a driveline and differential axle assembly to the vehicle traction wheels.

The Sensor Hardware

The sensor 20 is shown in plan view in FIG. 1 with its cover removed. The cover would enclose the elements that are visible in FIG. 1, and the cover would comprise a part of the sensor housing.

The sensor 20 comprises a plastic chassis or housing 36. The plastic is a light-weight, inexpensive material comprising an integral molded coil housing 36' and integral connector terminal housing portion 21. The plastic is formed by means of a molding process, and it is coated both inside and out with a copper plating, the inner coated surface being shown at 40, and the outer coated surface being shown at 40'. The copper layer, which is applied with an electroless process after the plastic is treated with a catalyst, is about 0.0005 inch thick. The catalyst will provide a surface on the plastic that will improve its adhesion properties during the plating. It forms a substrate for a nickel coating which also is applied to both the inner surface 40 and the outer surface 40' of the housing 36, as indicated in FIG. 7 as well as in FIG. 1. FIG. 1A shows a detailed cross-sectional view of a wall of the housing with the two metallic layers applied to the inner surface and the outer surface. The copper layer in FIG. 1A is identified by reference numeral 42, and the nickel layer is identified by reference numeral 44.

The interior of the housing 36 includes supporting ribs 46, seen in FIGS. 1 and 7, which support the circuit board 48 on which is positioned multiple integrated circuits schematically designated in block diagram form in FIG. 1. These circuits will be described with reference to FIGS. 9, 9A and 9B. Schematically illustrated also in FIG. 1 in outline form is the location 50 of an electronic microprocessor that will be described subsequently. The circuit board 48 and the microprocessor, as well as connector terminal assembly 52, are contained within the enclosure defined by the housing 36 and by the associated cover (not shown).

The cover may be a stamped sheet metal part with zinc plating with appropriate surface treatment, although it could be made also of the same coated material as the housing 36. When the cover is applied to the housing to enclose the microprocessor, the terminal assembly and the circuit board cover, it is electrically connected to the coating on the housing 36. This further improves the RFI protection. The cover may be glued or soldered to the housing, thus completely enclosing the electronic contents.

Preferably, the plastic of which the housing 36 is formed is a plastic material known as Radel Polyarysulfane which is manufactured and distributed by Amoco Performance Products, Inc. of Ridgefield, Conn.

This is a high temperature polymer material having suitable properties for injection molding. It has high thermal stability and good stress-crack resistance. The plastic is treated with a catalyst, as mentioned above, to allow the copper to firmly adhere to the plastic and form a substrate for the nickel plating.

Figure 3:
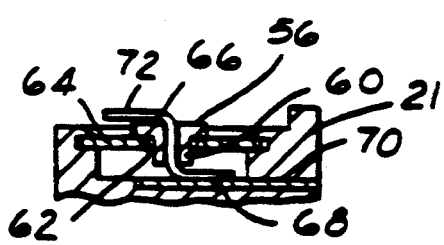
FIG. 3 is a cross-sectional view taken along the plane of section line 3—3 of FIG. 1.

Shown also in FIG. 1 in plan view is a series of three feed-through capacitors 54, 56 and 58. One such capacitor is shown in cross-sectional detail view in FIG. 3. It comprises a cylindrical ceramic element 60 received within an opening 62 in a metallic plate 64. A lead 66 is fed through a center opening in the ceramic 60 and is welded or soldered at 68 to the terminal part of a connector shown at 70. The connector is molded within the plastic housing portion 21 during the molding process. During assembly, the lead 66 is soldered to the terminal part of the connector 70, seen in FIGS. 3 and 4. Lead 66 then is soldered at 72 to lead extension 74, which is secured at 76 to a connector in the circuit board 48.

Figure 4:
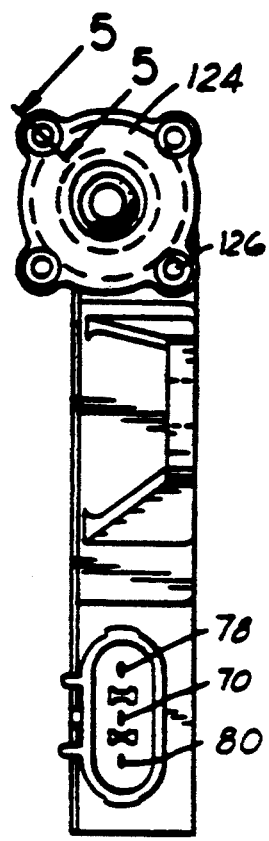
FIG. 4 is an end view as seen from the plane of section line 4—4 of FIG. 1.

The feed-through capacitors 54 and 58 are arranged in the same fashion, and they also include leads that are soldered to corresponding integral connectors seen in FIG. 4 at 78 and 80, respectively. These feed-through capacitors 54 and 56 also have lead extensions which are connected to the circuit board, as indicated at 82 and 84, respectively.

The metal plate 64 is soldered at its periphery to the nickel coating on the housing 36. The solder bead on the periphery of plate 64 is indicated in FIG. 1 at 86. A metal core in ceramic element 60 is in turn soldered to plate 64. The portion of the housing to which the plate 64 is soldered comprises a rectangular extension 88 formed integrally with the housing 36 during the molding of the housing 36.

The feed-through capacitors 54, 56 and 58 eliminate radio frequency interference and bypass any noise caused by RFI to the chassis ground. Capacitor 56 is situated at the signal voltage output for the sensor circuit of FIGS. 9 and 9A. Feed-through capacitor 54 provides an RF bypass for the voltage supply to the sensor, and feed-through capacitor 58 provides a RF insulating connection to ground on the output side of a voltage regulator on the input side of the circuit of FIG. 9.

The plated housing 36, which is a signal ground, may be connected to chassis ground through a ground strap, not shown. If the sensor is installed on a conductive surface such as the vehicle frame, the connection to chassis ground is through the conductive housing. If a ground strap is needed, we have found that a suitable strap design is a braided wire strap supplied by T. M. Morris Manufacturing Company, Inc. It is formed of tinned copper.

Two leads 90 and 92 are connected at their ends to the circuit board 48. Leads 90 and 92 are connected at the other end to a thermistor, best seen in FIG. 2. The thermistor is identified in FIG. 2 by reference numeral 94.

The thermistor comprises a stem 96 that extends through an opening 98, best seen in FIG. 6, which is formed during the process of molding the housing portion 18 for the sensing coil. Thermistor 94 measures the temperature of the fuel passing through the coil housing 36'.

An O-ring seal 100 surrounds the stem 94 and seals the interior of the housing portion 36' from the interior of the housing portion that is occupied by the circuit board. The interior of the housing 36' is generally cylindrical as shown at 102 in FIG. 2. It too is coated with copper and nickel as described with reference to the description of the housing 36.

As seen in FIG. 2, the thermistor 94 has an enlarged end cap 104 which is held in any suitable fashion (for example, by spring clip 106) against the interior surface 107 of the housing portion 36'. Also seen in FIG. 2 is sensing coil 108 which has multiple turns, one end of which is seen at 110. The end 110 extends through the molded plastic and terminates at pedestal 112 located within the housing 36 adjacent circuit board 48. Similarly, the other end of the coil 108 is molded within the housing portion 36' and terminates at the center of pedestal 14 similarly located within the housing 36. Extension lines 116 and 118 are connected to each of these ends of the coil and provide a connection with an integrated circuit on the circuit board 48.

Figure 5:
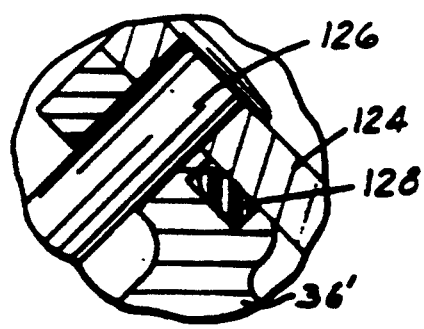
FIG. 5 is a partial cross-sectional view taken along the plane of section line 5—5 of FIG. 4.

The interior 102 of the housing portion 36' defines a fuel flow passage, each end of the passage communicating with a separate fuel feed line, as shown at 120 and 122 in FIG. 1. Each end of the housing portion 36' is sealed with a closure member, as seen in FIG. 5, at 124. Closure member 124 is in the form of a plate which is riveted by rivets 126 to provide a fluid-tight seal that prevents fuel leakage. At each end of the housing portion 36' is a seal ring 128 as seen in FIG. 5.

The housing 36 has mounting brackets 130 and 132 to permit its mounting on or near tank 18 or at some other suitable location in the vehicle, such as in the engine compartment. These brackets have openings that receive brass eyelets 131 and 133, respectively, which are electrically connected to the coating. If a ground strap is needed to establish a ground connection, the strap may be staked in an eyelet or otherwise connected to the housing.

The fuel that enters fuel line 120 passes through the opening 102 within which the sensing coil 108 is situated and exits through fuel line 122. It thus passes between the sensing coil 108 and the coating on the interior of opening 102, the latter acting as a capacitor plate and the coil 108 acting as an inductance coil for an oscillator circuit. The position of the coil 108 relative to the opening 102 is best seen in FIGS. 6 and 8. It thus is apparent that the entire sensor coating, including the coating around the sensing coil, provides radio frequency interference protection. That coating, together with the feed-through capacitors 54, 56 and 58, isolate the sensor from the environment outside the housing. Communication with the outside environment takes place only through the protected terminals at the capacitors 54, 56 and 58.

After the sensor hardware is assembled in the housing 36 and the system is checked and calibrated, the housing cavity is filled with a silicon gel. This protects the electronic elements, reduces or eliminates water and humidity problems, and helps to cushion vibrations.

Figure 9:
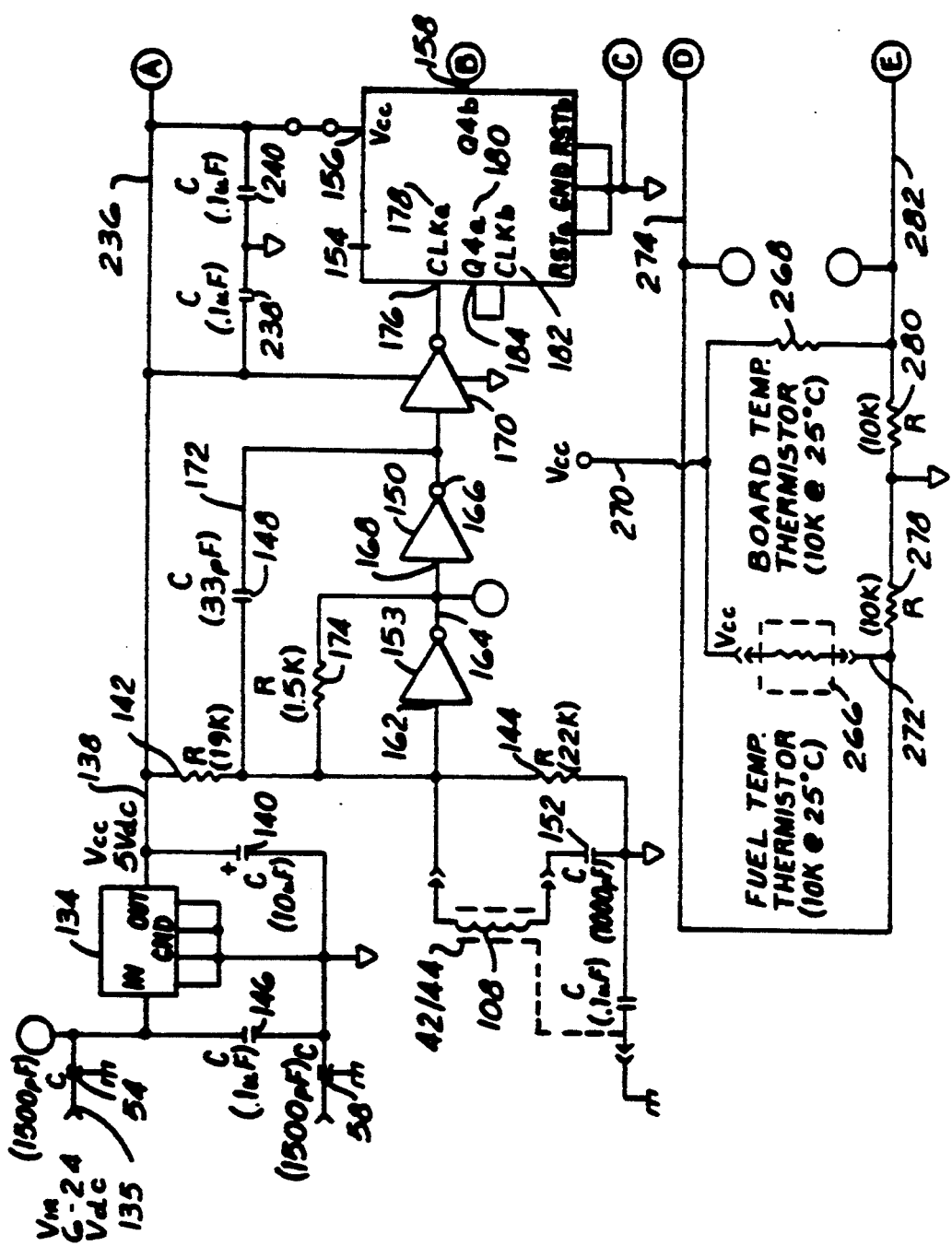
FIGS. 9 and 9A, taken together, show a schematic circuit diagram including the sensor of our invention and the related microprocessor circuit portions. The match prints for these figures are shown at A, B, C and D.
Figure 9A:
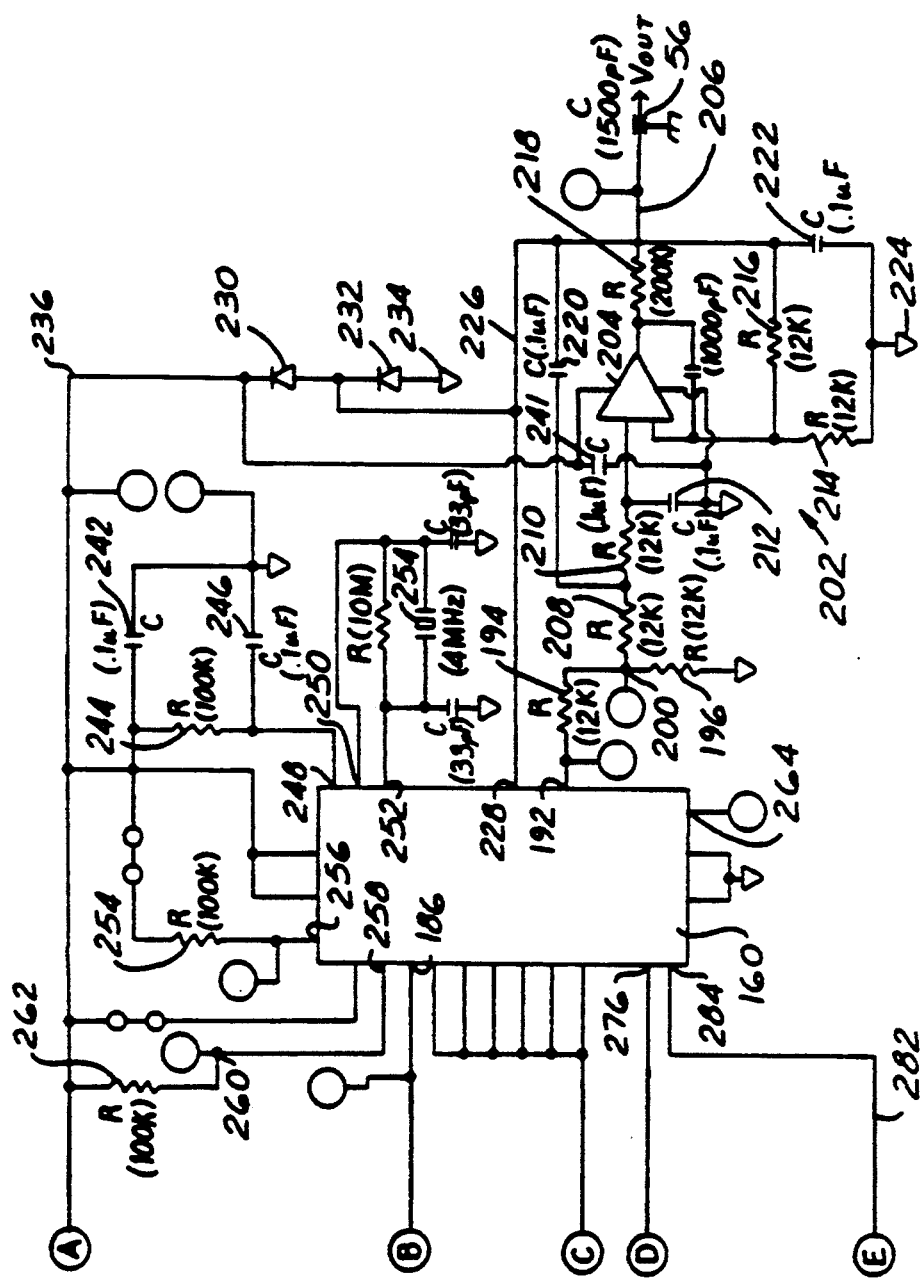

The Microprocessor Circuit of FIGS. 9 and 9A

In FIG. 9, power supply voltage enters the circuit at voltage regulator 134 from a dc source 135. Capacitor 54 provides radio frequency protection by providing a bypass RFI interference path to the chassis ground.

The input voltage (6 to 24 volts dc) passes through regulator 134 and develops a five-volt dc supply in line 138. The supply voltage is protected by a shunt-type capacitor 140, which extends to signal ground.

Resistors 142 and 144 establish a controlled supply voltage for the inverter circuit. It acts as a voltage divider which adjusts the threshold voltage for the sensing coil 108, which is about b 2.5 volts. A bypass capacitor 146 bypasses any high frequency noise that may be present on the supply voltage line at source 135.

Shown at 148 is a feedback capacitance of about 33 pF, which is interposed between the output side of inverter 150 and the driving side of the sensing coil 108.

Capacitor 152 prevents a direct shunt from the opposite side of the sensing coil 108. It blocks off dc voltage. It is a blocking capacitor that prevents a direct shunt from the inverter 153 to the signal ground, which is connected to capacitor 152. The copper and nickel coating shown at 42 and 44 surrounds the sensing coil 108 and, as schematically illustrated in FIG. 9, forms a capacitor plate which cooperates with the sensing coil to form an LC oscillating network that oscillates at a frequency around 18 MHz. The sensing coil also has distributive capacity between the coils, and this too has a tendency to establish an LC oscillating circuit. As mentioned earlier, the sensitivity of the signal that would be available with an oscillating system using only distributive capacitance might be only about 6 KHz which would be too low for present purposes. The parallel capacitance provided by the coating 42/44 provides greatly increased sensitivity. The sensitivity may be perhaps as high as 20 MHz for pure gasoline or as low as 10 MHz for pure methanol.

A frequency divider is shown at 154. The input to the frequency divider at pin 176 is divided by a factor of 256, so the frequency at the output of the frequency divider at point 158 is about 70–80 KHz. The frequency at pin 176, as mentioned above, may be as high as 18 MHz. The microprocessor, which is shown at 160, has a maximum useful frequency of about 100 KHz, so the input should be lower than that maximum design level.

The capacitance and the inductance of the sensing coil and coil housing coating establish a resonant frequency in accordance with the frequency equation:

$$f = \frac{1}{2\pi \sqrt{LC}}$$

The inductance factor L in this equation is approximately 2.7 microhenrys. The capacitance in this equation is approximately equal to 26 picofarads. For example, if the capacity should increase, the frequency will be reduced, and vice versa. The frequency is inversely proportional to capacitance.

Figure 10:
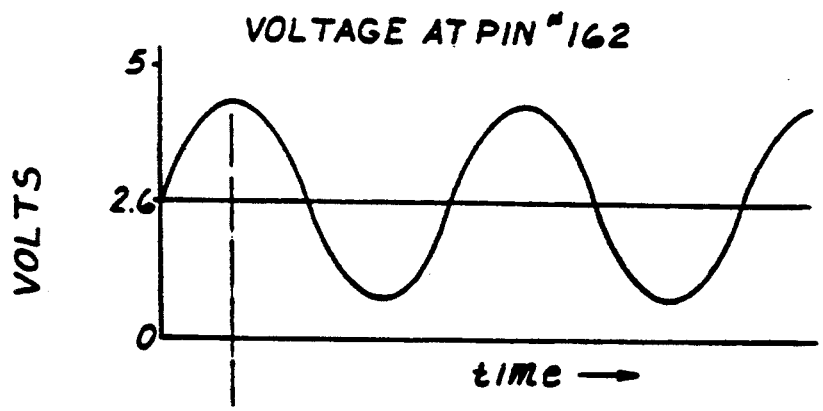
FIGS. 10 and 10A, 10B and 10C are voltage diagrams showing the characteristic voltage occurring, respectively, at the output side of the sensing coil of our invention, at the output side of the first inverter for the circuit of FIG. 9 at the input side of the second inverter for the circuit of FIG. 9 and at the output side of the second inverter.
Figure 10A:
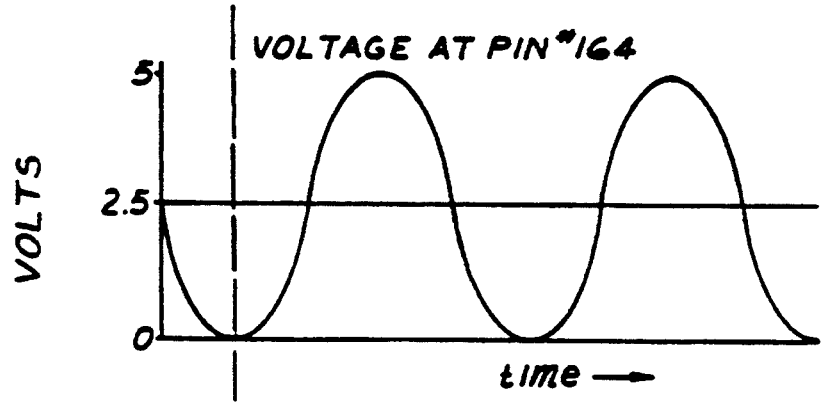

The signal waveform 162 to the inverter 153 is a sine wave. Inverter 153 inverts the frequency. This is illustrated graphically in FIGS. 10 and 10A where the voltage at the input 162 for the inverter 153 is compared to the voltage at the output 164. The high signal at pin 162 is reflected as a low signal at 164. Pin 162, for example, has 2.6 volts as its mean value, as seen in FIG. 10.

The sine wave voltage with a five volt peak and a zero volt minimum then is delivered to inverter 150, which inverts the wave. Thus the output side of the inverter at pin 166 will have a voltage of zero when the voltage at the input side at pin 168 is at 5 volts.

The wave then is inverted again by inverter 170. Between inverters 150 and 170 there is a feedback line 172 which contains a capacitor 148, previously described. This is a pickup back to the pin 162 on the input side of the inverter 153. The phase lag inherent in the inverter circuit is utilized by the capacitor 148 to help maintain the resonance of the sensing coil oscillations.

The resistor 174 is in parallel disposition with respect to the inverter 153 in order to introduce a slight phase shift at the instant that power is turned on, thereby facilitating the development of the resonant frequency of the sensing coil. Inverter 170 provides a buffer between the feedback circuit and the frequency divider 154. This prevents distribution of the useful signal to frequency divider 154 rather than to the capacitor 148 on start-up.

Figure 10B:
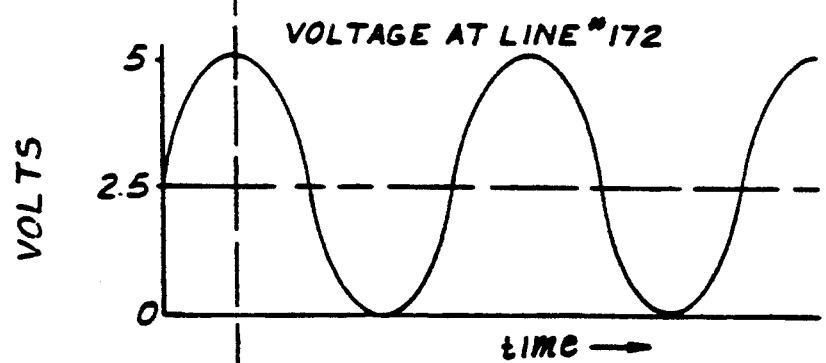
Figure 10C:
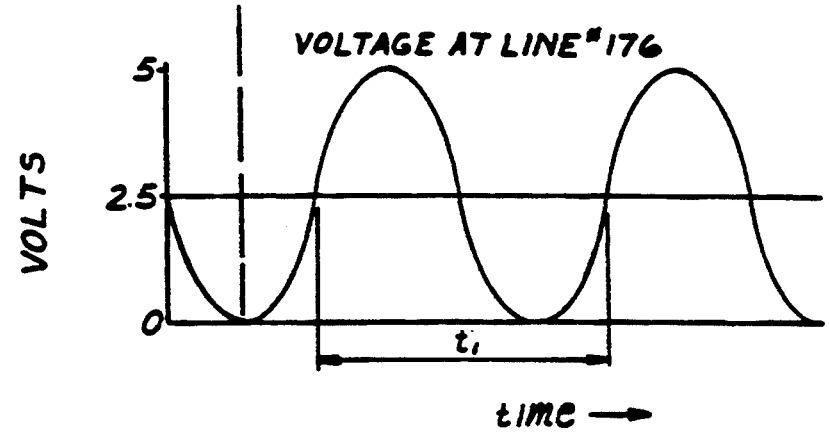
Figure 12:
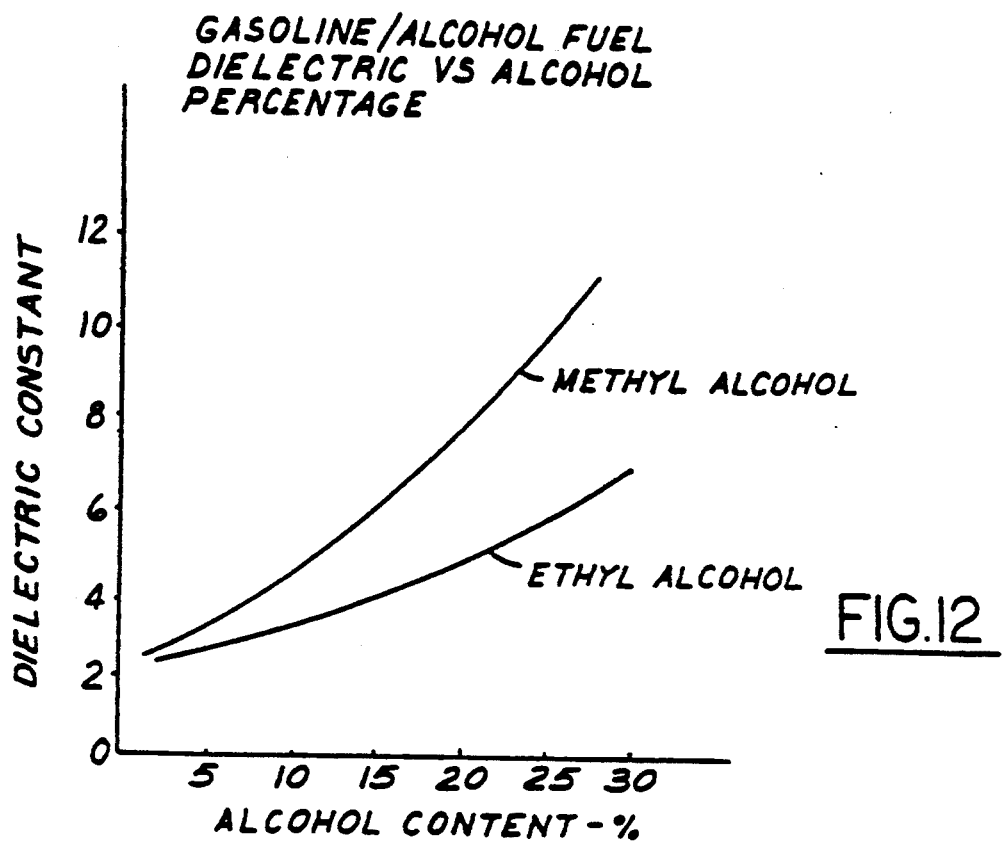
FIG. 12 is a diagram showing the relationship between methanol/alcohol content in the automotive fuel and the dielectric constant for the methanol/gasoline mixture.

The signal that is distributed to the frequency divider 154 at point 176 is a sine wave. The waveformat that point is shown in FIG. 10C. The phase of the waveform relative to the phase of the waveform in line 172, which is shown in FIG. 10B, can be seen by comparing FIG. 10C with FIG. 10B. The time for one complete wave cycle is shown as "t".

Figure 15:
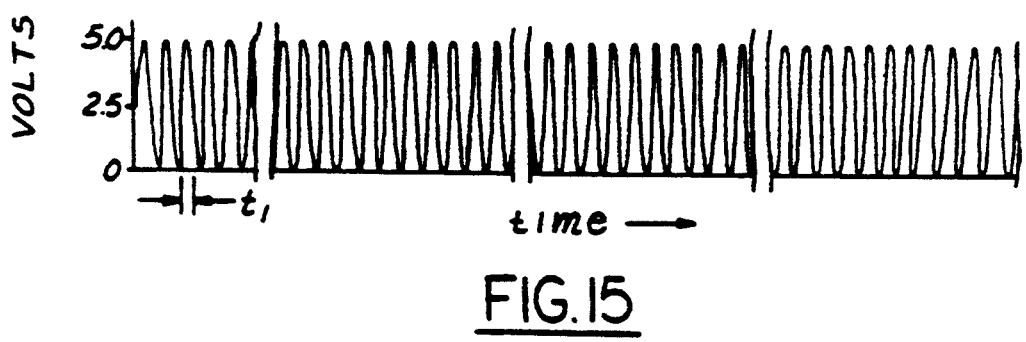
FIGS. 15 and 15A are diagrams of the waveforms at the input side and the output side, respectively, of the frequency divider of the circuit of FIG. 9.
Figure 15A:
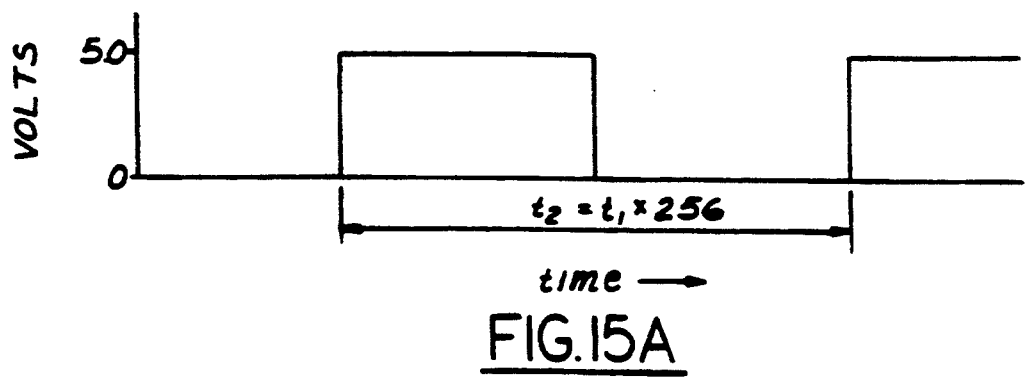

The divider 154 has a chip comprising two binary counters. The sine wave at point 176 acts as a counter for clock "a" at 178 of the frequency divider. The appearance of a signal at 176 will initiate clock pulses. When the pulses reach a count of 16, the most significant bit at 180 will go to 5 volts. The output of counter "a" upon reaching the full count, is fed to counter "b" at 182, which is the secondary counter. When counter output at 180 goes high upon reaching its final count, counter "b" will increment one count. Sixteen cycles of counter "a" will increment each count of counter "b". Thus, the total number of counts is $16^2$ or 256. At point 158, therefore, there are 256 counts at 0 volts followed by 256 counts at 5 volts. The frequency at pin 158, therefore, equals the frequency at pin 176 divided by the factor 256. This relationship between voltage, frequency and time is illustrated graphically in FIGS. 15 and 15A. The cycle time is changed by the divider 154 from $t_1$, to $t_2$ as shown in these figures.

The signal value at pin 158 is distributed to pin 186 of the microprocessor 160 and is stored in a temporary register shown schematically at 188 in FIG. 9A. The program counter will indicate a register that the CPU uses. The CPU fetches the data from temporary memory and compares it to a table value located at another register in the memory after performing a calculation based upon an algorithm stored in memory. The result of the computation developed by the CPU and fetched from the appropriate memory location is transferred to the signal output pin 192. This is a pulse length modulation signal. The length of the signal is varied at the five-volt level. The length of the five-volt square wave changes depending upon the result of the calculation based on the algorithm, thus effecting the correct duty cycle at point 192 on the output side of the processor.

The main control algorithm used by the CPU is expressed as:

$$eth\ nol = \frac{\frac{1}{(K)L_x}[f + K_L(T_b - T_{ref})]^2 - (K_{OC}^+)}{A^+(T_{fuel})}$$

where f=frequency, $T_b$=board temperature, and $T_{fuel}$=fuel temperature. These are the variables involved. The other factors in the algorithm are constants that are empirically determined.

The output at point 192 is distributed to a voltage divider comprising resistors 194 and 196, the latter being connected to signal ground at 198. The voltage at point 200 equals the resistance at 196 divided by the sum of the resistances at 196 and 194 times the voltage at point 192. If the resistances at 194 and 196 are equal, the voltage at point 200 is one-half the voltage at point 192, but it has the same duty cycle. The only change is in the amplitude of the signal. This reduction in the voltage is necessary because of the function of the low pass filter circuit generally shown at 202, which includes operational amplifier 204.

The low-pass filter multiplies the signal by two giving an output signal of unity at point 206, assuming a 50 percent duty cycle at point 200. Resistors 208 and 210 and capacitor 212 convert the pulse width modulated signal to a dc signal. It averages the signal values at resistors 208 and 212 and at capacitor 212, and they cooperate with resistors 214 and 216 and with resistor 218 and capacitor 220 to define a converter, which is a low-pass filter. The function of a low-pass filter of this kind is generally known in the art and need not be described in particular further.

Capacitor 222 is a bypass capacitor to bypass electronic noise at point 206 to signal ground at 224.

The signal made available at 206 is a dc voltage. It is this signal that is seen by the powertrain microprocessor controller 24 described previously.

Line 226 provides a signal feedback path to point 228 of the microprocessor 160. The processor will compare the voltage that is seen at point 206 and distributed through line 226 and compares it to a value in memory, which is the value that the voltage should equal. The actual voltage then is adjusted for any error that is encountered as the signal passes through the low-pass filter. This corrected signal then is the signal that finally appears at output point 206.

An over-voltage protection and an under-voltage protection are achieved by paired diodes 230 and 232. Diode 232 has one of its sides grounded to signal ground point 234. The output side of the second diode 230 is connected directly to supply line 236, which leads to the five volt supply at the regulator 134. Diodes 230 and 232 prevent voltage spikes from damaging the processor 160. It clips or truncates the peak voltage. If the voltage at 206 exceeds about 5.7 volts, the diode 230 is triggered and becomes conductive, which connects the feedback line 226 directly to the five volt supply. Paired diode 232 prevents development of negative voltages below a value of about −0.6 volt below ground value.

Regulator 136 regulates the voltage supply to five volts in line 138. Capacitor 140 is used for the purposes of stability and to prevent oscillations at the output side of regulator 134.

At each of the integrated circuits described with reference to FIGS. 9 and 9A, there is a protective capacitor which acts as a bypass to cut the noise. Thus, capacitor 238 is provided to protect the inverter 170, capacitor 240 is provided to protect the binary counter 154, and capacitor 242 protects the microprocessor 160. The operational amplifier 204 is protected by capacitor 241, which has one side connected to signal ground.

Figure 9B:
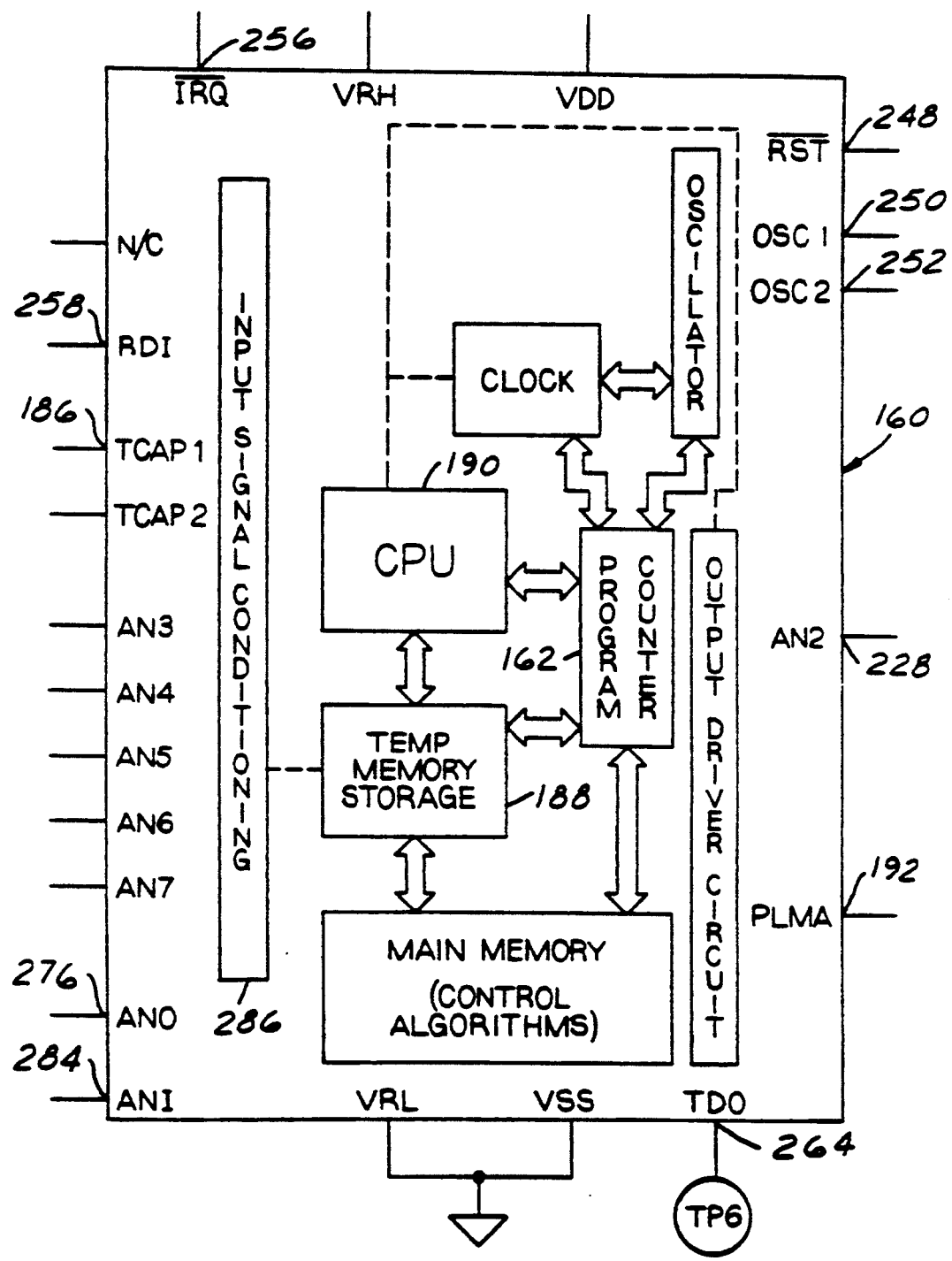
FIG. 9B is a schematic representation of the architecture of the microprocessor used in the circuit diagram of FIGS. 9 and 9A.

Resistor 244 and capacitor 246 together define an independent RC network for pin 248 of the microprocessor 160 of FIG. 9B. This provides a power-on reset for the microprocessor. This starts the microprocessor when the power first is turned on, which permits the processor to address certain locations in the memory where the operational software is stored.

At the instant that the power supply is turned on, the voltage at point 248 is at zero volts. The voltage at point 248 begins to increase due to the capacitor 246 becoming charged. The rate of charge is calculated as t=RC. This provides the required "low" voltage signal after "power-up" to reset the microprocessor.

Pins 250 and 252 for the microprocessor 160 see oscillator frequency from a resonator shown at 254. The oscillating voltage at points 250 and 252 cause the program counter of the processor 160 to increment at a rate of four Mhz. Each time the program counter increments, the instruction sets are sequentially executed step by step as the functions dictated by the algorithms are carried out.

A pull-up resistor 254 is connected to the processor at point 256 This prevents an interrupt request signal, "low" voltage, by pulling point 256 "high" to five volts.

Input point 258 is merely a point at which input data may be entered into the microprocessor from an external source at point 260. The voltage at point 258 is brought up to five volts by protective resistor 262, which functions like resistor 254. Appropriate data can be entered into the processor through point 260 to change its calibration as desired. The data can be retrieved from the microprocessor at point 264 for diagnostic purposes. Points 264 and 258 thus provide a through channel for the flow of information in a bit stream to and from the processor during calibration as data is entered and retrieved at these points. For example, the frequency range that is calibrated for a given fuel at the sensor coil should be received at point 264; but if it is not the same as the calibration expected, adjustments can be made by entering correcting data at point 258.

Shown in FIG. 9 are two thermistors. These are indicated at 266 and 268. The five volt supply enters the thermistors from line 270. The voltage at the output side of thermistor 266 which is seen at 272, is distributed through line 274 to pin 276 of the microprocessor 160. The voltage at point 276 changes with temperature of the fuel. The thermistor 266 was described previously and identified generally in FIG. 2 by reference numerals 94 and 96. The fuel temperature is one of the variables received by the microprocessor, and appropriate algorithms in the memory section of the processor will be used to alter the output signal at point 228 to compensate for changes in the dielectric constant as the temperature of the fuel changes.

Thermistor 268 measures circuit board temperature. It is surface mounted on the circuit board and is one of a well known variety of resistors known as MELF resistors. The resistance of the MELF sensor changes with temperature. Thermistor 266 and resistor 278 form a voltage divider, the output of which is distributed through line 274. Similarly, thermistor 268 and resistor 280 form another voltage divider, and its output is distributed to line 282 connected to analog channel 284. Line 274 is connected to an analog channel corresponding to point 276. These communicate with an analog-to-digital converter within the input signal conditioning portion of the microprocessor, as seen in FIG. 9B.

The dielectric constant of methanol changes with fuel temperature and the reading is affected by board temperature. The processor will use the information regarding both temperature changes to cause a phase shift in the signal that is seen at point 200.

Thermistor 268 may be mounted on a circuit board 48 shown at FIG. 1 at any convenient location, such as the location 286 in FIG. 1.

The signal that is distributed by the microprocessor to point 206 is received by the powertrain controller as described previously. The appropriate air/fuel ratio is determined by the powertrain controller using information indicating a relationship between the percentage oxygen in the fuel and the heat content of the fuel for each particle of fuel passing through the fuel line.

Figure 13:
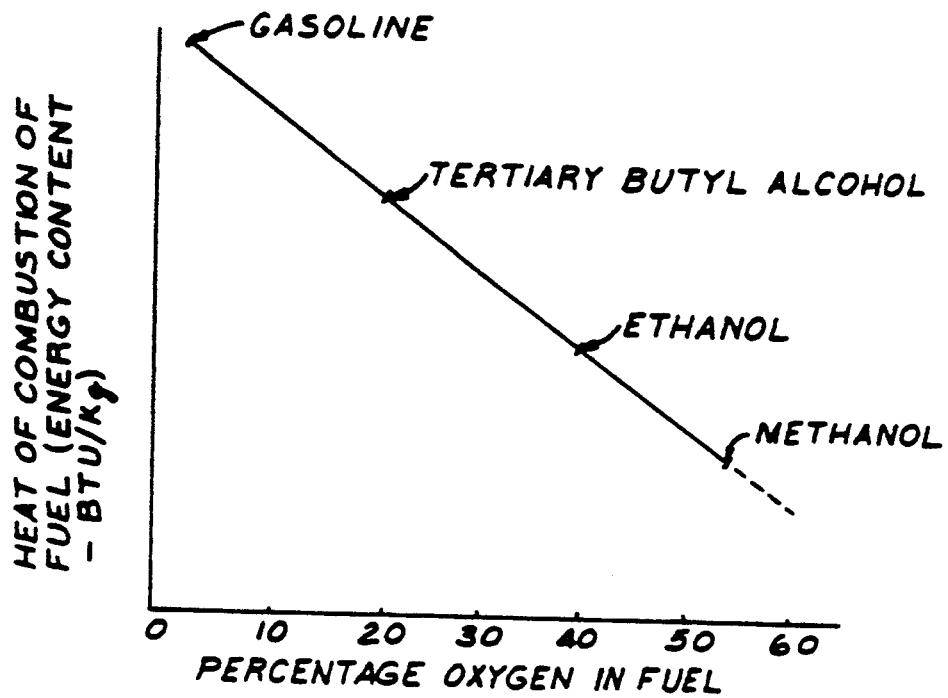
FIG. 13 is a chart that shows the relationship between oxygen content in the fuel and the heat of combustion of the fuel.
Figure 14:
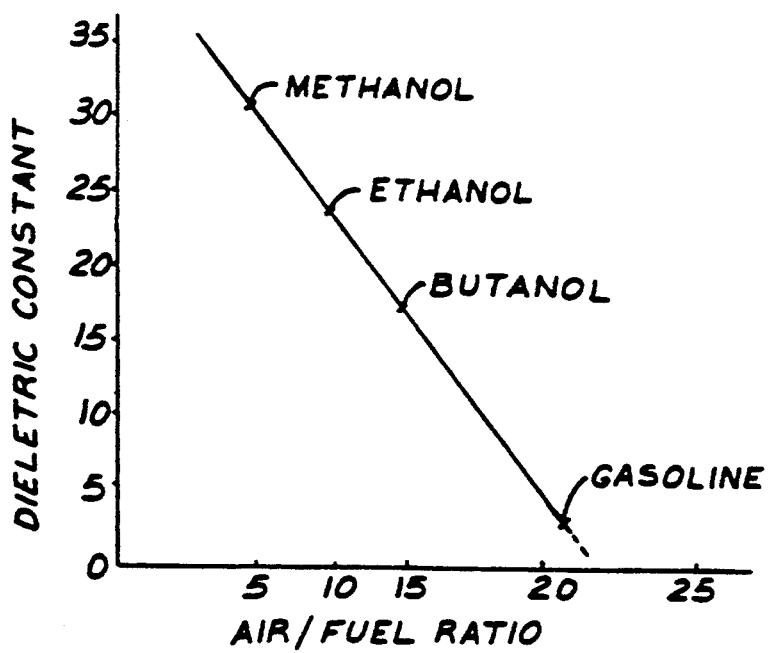
FIG. 14 is a graphic illustration of the relationship of dielectric constant to air/fuel ratio developed by the powertrain controller.

It has been found that the relationship between the percentage oxygen in the fuel and the heat content is determined by the source of the oxygen in accordance with the linear relationship illustrated in FIG. 13, regardless of whether the oxygen is supplied with the additive methanol or some other additive. The linear relationship is generally as indicated in FIG. 13. Using the information of FIG. 13 and the relationship between the dielectric constant of a particle of fluid with alcohol additives, as illustrated in FIG. 14, the processor can determine, together with other information received from other powertrain sensors, an appropriate air/fuel ratio and an appropriate spark timing for the engine. As seen in FIG. 14, each of several alcohol fuels known in the industry, as well as gasoline, has an independent dielectric constant. The value of that constant varies generally linearly with respect to air/fuel ratio.

Figure 16:
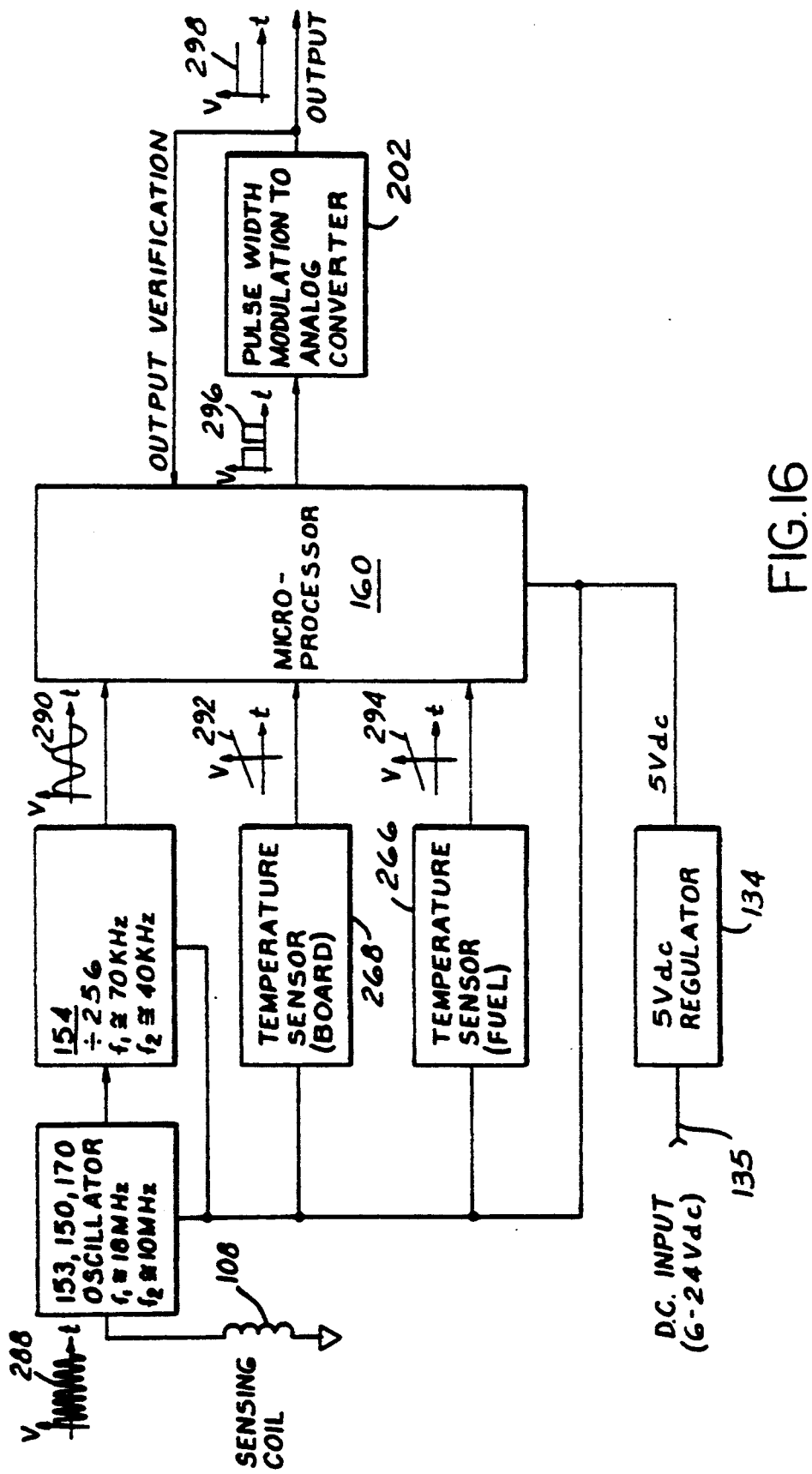
FIG. 16 is a system block diagram of the principal elements of the circuit of FIGS. 9 and 9A.

FIG. 16 is a block diagram of the microprocessor circuit of FIGS. 9 and 9A. The sensing coil 108, the inverter 153 and the inverter 150 of FIG. 9 have been identified in FIG. 16 as an oscillator in block diagram form. The input to the oscillator is indicated to be a high frequency sine wave in FIG. 16, as shown by the waveform diagram 288 in FIG. 16. The output from the oscillator, which is designated by the reference numerals 153, 150 and 170, is distributed to the frequency divider 154. The frequency developed by the oscillator is about 18 MHz for gasoline with zero percent methanol. The frequency for a fuel consisting of 100 percent methanol is indicated to be approximately 10 MHz. For a mixture of alcohol and gasoline with a concentration of methanol between zero and 100 percent, the frequency developed by the oscillator would be between 10 and 18 MHz. After the frequency divider acts on the output of the oscillator as described previously, the resulting frequency, as indicated in FIG. 16, would be between 40 KHz and 70 KHz, depending on the alcohol concentration.

FIG. 16 also shows the waveform for the signal on the output side of the voltage divider, the waveform being designated by reference numeral 290.

The board temperature sensor 268 is connected to the five volt supply developed by the regulator 134. The output side of the temperature sensor 268 develops a signal that is variable substantially linearly with respect to time as indicated in the voltage signal diagram shown at 292. A similar voltage diagram for the fuel temperature sensor 266 is indicated on the output side of the sensor 266 as shown in the diagram designated by the numeral 294.

As explained previously, the output of the microprocessor 160 is a pulse-width modulated signal, as indicated by the waveform diagram designated by reference numeral 296 in FIG. 16. This is substantially a square wave voltage which is input to the low-pass filter circuit which functions as a pulse-width modulation to analog converter. That circuit is shown at 202 in FIG. 16. The output side of the circuit 202 is a dc voltage output as shown by the voltage diagram 298 in FIG. 16.

Figure 17:
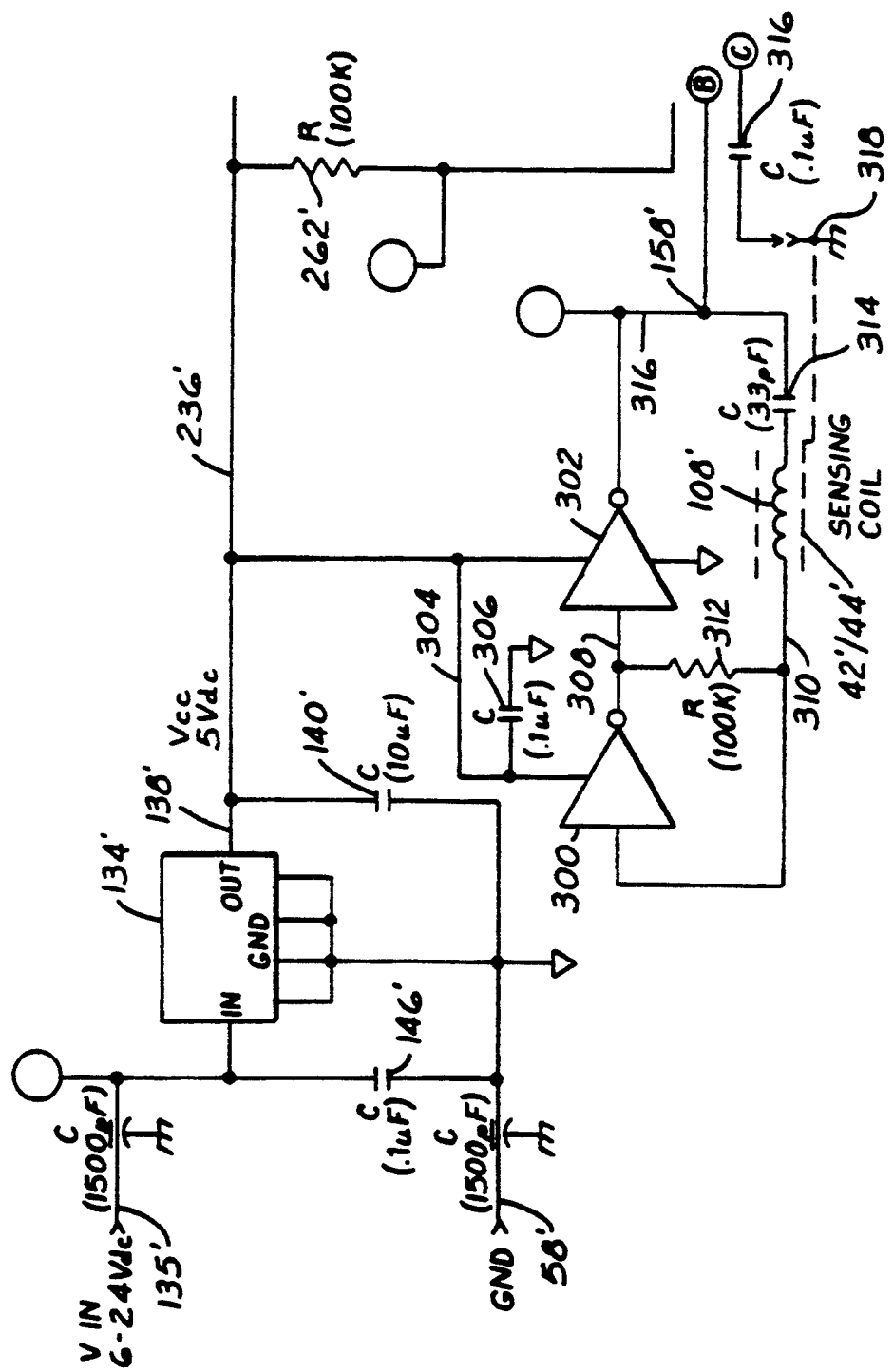
FIG. 17 is a partial representation of a microprocessor circuit for an alternate embodiment of our invention, including two astable multivibrators for establishing an oscillating frequency in an RC network that includes a sensing coil corresponding to the sensing coil of FIG. 9.

Alternate Embodiment of FIG. 17

An alternate embodiment of our invention includes an oscillator circuit comprising two Schmitt inverters which function as astable multivibrators. These are situated at the input side of the microprocessor and develop a square wave output that is used as the input to the microprocessor. Because the frequency of the square wave is substantially less than the frequency of the sine wave developed with the circuit of FIG. 9, it is possible to simplify the overall circuit because the voltage divider that would be required in a circuit of the type shown in FIG. 9 can be eliminated.

In FIG. 17, we have illustrated a microprocessor circuit and an oscillator network of lower frequency. Since the circuit does not require a voltage divider corresponding to the voltage divider 154 in FIG. 9, the output of the oscillator network is fed directly to the microprocessor.

The circuit of FIG. 17 comprises an astable multivibrator having inverters 300 and 302. The power supply for inverter 300 is shown at 304. This is connected to the five-volt dc supply at 138'.

The elements of the circuit of FIG. 17 that are common to the circuit of FIG. 9 are identified by reference characters similar to those used in FIG. 9, although prime notations are added. Thus, the source for the five-volt supply for the circuit of FIG. 17 is the voltage regulator 134'.

A protective capacitor 306 connected to ground avoids electromagnetic interference.

The output side of inverter 300 is connected to the input side of inverter 302 by line 308. The input side of inverter 300 is connected to sensing coil 108 through line 310, the latter being connected to line 308 by resistor 312.

One side of the sensing coil 108' is connected to the output side of inverter 302 by capacitor 314 located in line 316, the latter being connected to point 158' which serves as an input point for the microprocessor.

The input signal conditioning portion 286 of the microprocessor 160 is able to convert the square wave input to useful information that may be acted upon by the CPU 190 because the operational software stored in memory is tailored to this digital form. Other operational software in memory is tailored to the sine wave form described with reference to FIGS. 9 and 9A.

The plating, which corresponds to the plating 42 and 44 of the embodiment of FIG. 9, is shown at 42' and 44' and is grounded at 318.

Figure 18:
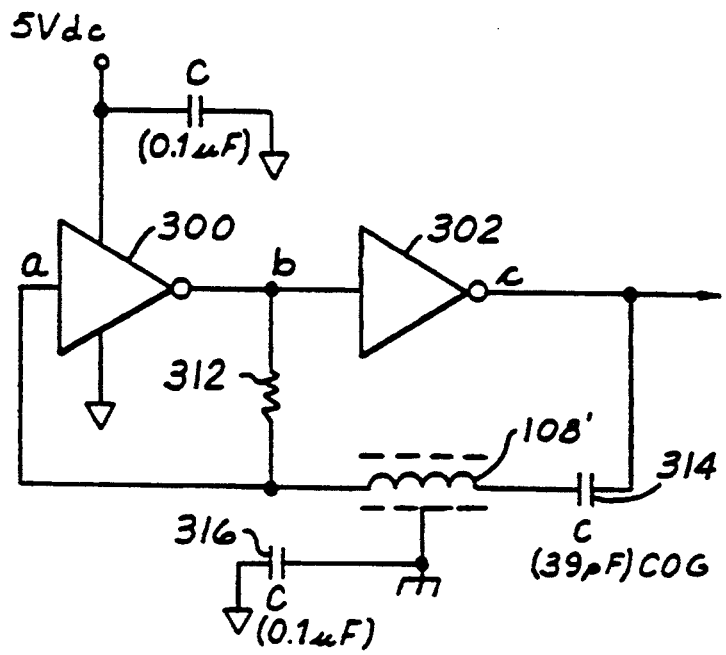
FIG. 18 is a detail view of the oscillator circuit of FIG. 17 including paired Schmitt inverters.

In FIG. 18, we have shown an enlargement of the network for the two inverters 300 and 302. These elements form an oscillator which produces the waveforms illustrated in FIGS. 18A, 18B, 18C and 18D. The oscillator comprises the paired inverters and an RC network, the latter consisting of resistance 312 and capacitor 314.

The high level digital "1" state for the astable multivibrator circuit of FIG. 18 is 5 volts and the low level digital "zero" state is zero volts.

If it is assumed that at any instant the voltage at point "a" which is an insulated gate for the inverter 300, is at 5 volts, the corresponding voltage at point "b" between the inverters is at zero volts. No current flows through the input for inverter 300. The current path from point "b" to point "c" is available, but there in no current path available between points "a" and "b". When the voltage at point "a" is high, it is greater than the inverter switching voltage, which may be about 3.6 volts. Thus, there is a current created across resistor 312 when the voltage at point "a" is high. Thus, the capacitor 314 begins to charge. As the voltage of the capacitor at 314 rises, the voltage at point "a" drops; and when it reaches the trigger point, the inverter 300 switches digital states. Thus, the voltage at point "a" becomes low and the voltage at point "b" becomes high. Likewise, the voltage at point "c" on the output side of the inverter 302 becomes low.

Figure 18A:
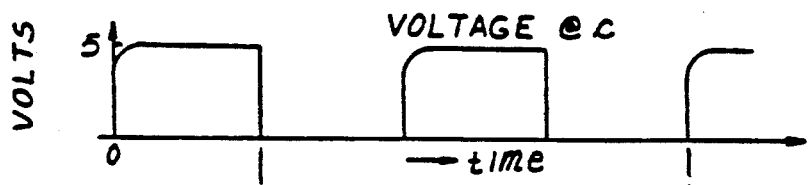
FIG. 18A is a waveform diagram for the voltage at the output of the oscillator circuit of FIG. 18.
Figure 18B:
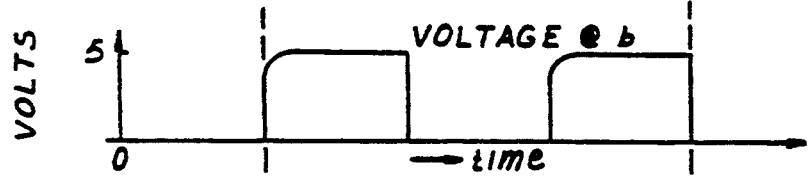
FIG. 18B is a waveform diagram for the voltage at a point between the inverters of FIG. 18.
Figure 18C:
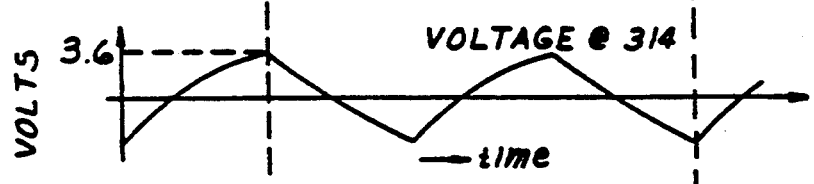
FIG. 18C is a waveform diagram for the voltage at the capacitor of the oscillator circuit of FIG. 18.

The voltage at the capacitor 314 is illustrated in FIG. 18C. It in seen that it rises from a negative value of −2.5 volts to a positive value of +2.5 volts until the inverters change state. The voltage at the capacitor 314 then decays until it reaches its original negative voltage, at which time the inverters change state. The voltage pattern at the capacitor 314 then is repeated.

Figure 18D:
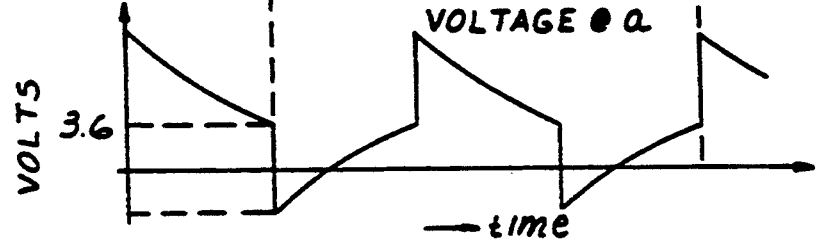
FIG. 18D is a waveform diagram for the voltage at the input side of the first inverter of the oscillator circuit of FIG. 18.

The waveform at point "a" is illustrated in FIG. 18D. It begins, for example, at a high value and decreases as the capacitance of the capacitor 314 builds up. It continues to decrease until the switch point of 3.6 volts is reached, at which time a change in state occurs and the voltage becomes low. The corresponding voltage that appears at point "c" is zero, as indicated in FIG. 18A, which is a plot of the waveform at point "c".

The waveform for the voltage at point "b" is indicated in FIG. 18B. The waveforms of FIGS. 18A and 18B are square waves that are 180 degrees out of phase, one with respect to the other.

The rate of voltage build-up is determined by the resistance (R1) for resistor 312 and the capacitance (Cl) for capacitor 314. The capacitance of the coil (CL1) itself, which is a distributive capacitance, and the capacitance of the capacitor 314 are additive. Thus, the frequency is equal to 1 divided by the quantity Rl(Cl+CL1).

The oscillating frequency of the circuit of FIG. 18, unlike the frequency for the oscillator of FIG. 9, is not a resonant frequency. Rather, it is a frequency that depends on the values of the circuit timing variables, which are the resistance at 312 and the capacitance at 314 as well as the distributive capacitance of the coil.

This frequency is much lower than the frequency that exists for the oscillator of FIG. 9. For example, the output frequency for gasoline with zero percent methanol would be approximately 70 KHz and would be approximately 40 KHz for pure methanol. The frequency for methanol concentrations between these extremes would fall within the range of 70 KHz to 40 KHz. There is no need, therefore, to divide the oscillator output frequency since the values for frequency are well within the tolerance limits of the microprocessor.

The coil 108' is surrounded by the plating which forms a capacitor plate, and the plating is protected in the usual fashion by a capacitor, as shown at 316, one side of which is grounded to signal ground.

Having described a preferred embodiment of our invention, what we claim and desire to secure by United States Letters Patent is:

1. A fuel sensor for measuring concentration of an additive to liquid fuel in a fuel system for an internal combustion engine for a vehicle, said vehicle and said engine having a chassis ground, said sensor comprising an electronic oscillator circuit including a capacitor and an inductance coil exposed to said fuel, said oscillator circuit having an oscillating frequency that is functionally related to additive concentration as said fuel acts as a dielectric, a sensor signal voltage source, voltage regulator means connected to said source for establishing a predetermined voltage input for said oscillator circuit;

a frequency divider circuit means connected to the output side of said oscillator circuit for reducing said oscillator frequency;

an electronic microprocessor means having a signal input portion connected to the output side of said frequency divider circuit means, said microprocessor means being adapted to develop a pulse width modulated signal having a duty cycle that is a function of the output frequency of said frequency divider circuit means; and a pulse width modulation to analog converter means connected to a signal output portion of said microprocessor means for establishing a direct current output signal that is functionally related to said pulse width modulated signal.

2. The combination as set forth in claim 1 wherein said fuel sensor includes a fuel temperature transducer means exposed to said fuel and connected to said signal input portion of said microprocessor means whereby said pulse width modulated signal output of said microprocessor means is functionally related to fuel temperature.

3. The combination as set forth in claim 1 wherein said pulse width modulating to analog converter means includes a low pass filter circuit for developing a direct current voltage signal and an operational amplifier circuit means for enhancing and stabilizing said direct current voltage signal.

4. The combination as set forth in claim 2 wherein said pulse width modulating to analog converter means includes a low pass filter circuit for developing a direct current voltage signal and an operational amplifier circuit means for enhancing and stabilizing said direct current voltage signal.

* * * * *